(12) United States Patent
Kovi et al.

(10) Patent No.: US 11,034,714 B2
(45) Date of Patent: *Jun. 15, 2021

(54) PROCESS OF MAKING REGADENOSON AND NOVEL POLYMORPHS THEREOF

(71) Applicant: APICORE US LLC, Canonsburg, PA (US)

(72) Inventors: Ravishanker Kovi, Monroe, NJ (US); Jayaraman Kannapan, Gujarat (IN); Piyush D. Fadadu, Gujarat (IN); Ashish Naik, Piscataway, NJ (US)

(73) Assignee: Apicore US LLC

( * ) Notice: Subject to any disclaimer, the term of this patent is extended or adjusted under 35 U.S.C. 154(b) by 0 days.

This patent is subject to a terminal disclaimer.

(21) Appl. No.: 16/553,372

(22) Filed: Aug. 28, 2019

(65) Prior Publication Data

US 2020/0017539 A1 Jan. 16, 2020

Related U.S. Application Data

(63) Continuation of application No. 15/013,887, filed on Feb. 2, 2016, now Pat. No. 10,442,832.

(60) Provisional application No. 62/187,977, filed on Jul. 2, 2015, provisional application No. 62/112,680, filed on Feb. 6, 2015.

(51) Int. Cl.
*C07H 19/16* (2006.01)
*C07H 19/167* (2006.01)
*C07H 1/00* (2006.01)

(52) U.S. Cl.
CPC ............... *C07H 19/16* (2013.01); *C07H 1/00* (2013.01); *C07H 19/167* (2013.01)

(58) Field of Classification Search
CPC .............................. C07H 19/16; C07H 19/167
See application file for complete search history.

(56) References Cited

U.S. PATENT DOCUMENTS

| | | | |
|---|---|---|---|
| 2,500,329 | A | 3/1950 | Steitz, Jr. |
| 6,403,567 | B1 | 6/2002 | Zablocki |
| 6,514,949 | B1 | 2/2003 | Linden |
| 7,671,192 | B2 | 3/2010 | Zablocki et al. |
| 7,732,595 | B2 | 6/2010 | Zablocki et al. |
| 7,956,179 | B2 | 6/2011 | Zablocki et al. |
| 8,106,183 | B2 | 1/2012 | Zablocki et al. |
| 8,268,988 | B2 | 9/2012 | Zablocki et al. |

(Continued)

FOREIGN PATENT DOCUMENTS

| | | |
|---|---|---|
| IN | 1470/MUM/2011 A | 12/2012 |
| IN | 1226/MUM/2013 A | 3/2013 |

(Continued)

OTHER PUBLICATIONS

International Search Report and Written Opinion for corresponding PCT Application No. PCT/US2016/016217, 8 pages, dated Apr. 14, 2016.

(Continued)

*Primary Examiner* — Bahar Craigo

(57) ABSTRACT

Novel processes for making the N-pyrrazole substituted 2-adenosine derivative regadenoson and a novel polymorph thereof. The novel polymorph of regadenoson designated form H and drug substances and pharmaceutical compositions including the novel polymorph H are disclosed.

10 Claims, 2 Drawing Sheets

(56) References Cited

U.S. PATENT DOCUMENTS

| | | |
|---|---|---|
| 8,524,883 B2 | 9/2013 | Zablocki et al. |
| 8,859,522 B2 | 10/2014 | Wooldridge et al. |
| 9,085,601 B2 | 7/2015 | Zablocki et al. |
| 9,809,617 B2 | 11/2017 | Lui et al. |
| 2014/0045781 A1 | 2/2014 | Wooldridge et al. |
| 2014/0194615 A1 | 7/2014 | Kvapil et al. |
| 2014/0213539 A1 | 7/2014 | Zablocki |
| 2014/0323712 A1 | 10/2014 | Kvapil |
| 2016/0024137 A1 | 1/2016 | Grisenti et al. |
| 2016/0115191 A1 | 4/2016 | Rangisetty et al. |

FOREIGN PATENT DOCUMENTS

| | | |
|---|---|---|
| IN | 3310/MUM/2012 A | 11/2013 |
| IN | 1219/MUM/2013 A | 4/2015 |
| IN | 1831/CHE/2013 A | 5/2015 |
| IN | 565/MUM/2014 A | 9/2015 |
| IN | 3485/MUM/2015 A | 9/2015 |
| IN | 3428/MUM/2015 A | 10/2015 |
| WO | 2007092372 A1 | 8/2007 |
| WO | 2008143667 A1 | 11/2008 |
| WO | 2012149196 A1 | 11/2012 |
| WO | 2013026424 A1 | 2/2013 |
| WO | 2014068589 A2 | 5/2014 |
| WO | 2014167046 A1 | 10/2014 |
| WO | 2014177119 A1 | 11/2014 |
| WO | 2014207758 A2 | 12/2014 |
| WO | 2015085497 A1 | 6/2015 |
| WO | 2016126734 A1 | 8/2016 |
| WO | WO2017042837 A2 * | 3/2017 |

OTHER PUBLICATIONS

He, X et al. Controlled cystallization and granulation of non-scale beta-Ni(OH)2 cathode materials for high power Ni-MH batteries. Journal of Power Sources, vol. 152, pp. 285-290; p. 286, col. 1, paragraph 3, (2005).

Thannhauser, SJ et al. Studies of Acetal Phospholipides of Brain. The Journal of Biological Chemistry, vol. 188, pp. 417-421; p. 418, paragraph 3, (Jan. 1951).

* cited by examiner

PROCESS OF MAKING REGADENOSON AND NOVEL POLYMORPHS THEREOF

CROSS-REFERENCE TO RELATED APPLICATIONS

This application is a continuation of U.S. patent application Ser. No. 15/013,887, filed Feb. 2, 2016, which claims the benefit of U.S. Provisional Patent Application No. 62/112,680 filed Feb. 6, 2015, and U.S. Provisional Patent Application No. 62/187,977 filed Jul. 2, 2015, the entireties of which are incorporated herein by reference.

FIELD OF INVENTION

The present invention relates to novel processes for making the N-pyrrazole substituted 2-adenosine derivative regadenoson and a novel polymorph thereof.

BACKGROUND OF THE INVENTION

Regadenoson, having the chemical name 1-{9-[4S, 2R, 3R, 5R)-3,4-dihydroxy-5-(hydroxymethyl)oxalan-2-yl]-6-aminopurin-2-yl]pyrazol-4-yl)-N-methylcarboxamine, is currently used as a coronary vasodilator.

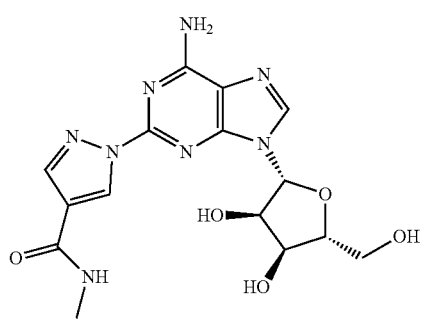

(I)

SUMMARY OF THE INVENTION

Embodiments of the present disclosure relate to novel processes for making regadenoson and a novel polymorph thereof. Compounds disclosed herein may be used as coronary vasodilators as well as therapeutics for any other disorders mediated by $A_{2A}$ receptors.

In accordance with an embodiment, a process for the preparation of [(1-{9-[4S, 2R, 3R, 5R)-3,4-dihydroxy-5-(hydroxymethyl)oxalan-2-yl]-6-aminopurin-2-yl]pyrazol-4-yl)-N-methylcarboxamine] namely regadenoson of Formula (I)

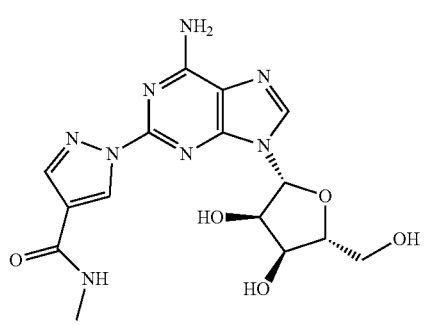

(I)

includes reacting a compound of the formula (II) ethyl 1-(6-amino-9-((2R,3R,4S,5R)-3,4-dihydroxy-5-hydroxymethyl)tetrahydrofuran-2-yl)-9H-purin-2-yl)-1H-pyrazole-4-carboxylate

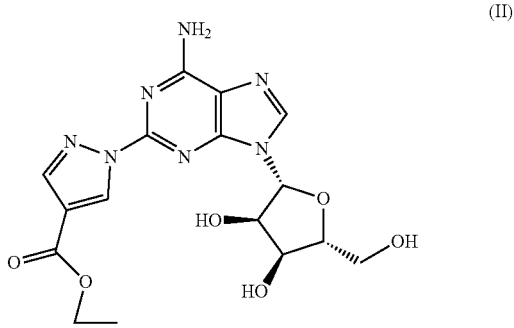 [SMILES: CCOC(=O)c1cnn(-c2nc(N)c3ncn([C@@H]4O[C@H](CO)[C@@H](O)[C@H]4O)c3n2)c1]

(II)

with aqueous methylamine solution.

In another embodiment, a process for the preparation of formula (II) ethyl 1-(6-amino-9-((2R,3R,4S,5R)-3,4-dihydroxy-5-hydroxymethyl)tetrahydrofuran-2-yl)-9H-purin-2-yl)-1H-pyrazole-4-carboxylate includes reacting a compound of the formula (III)

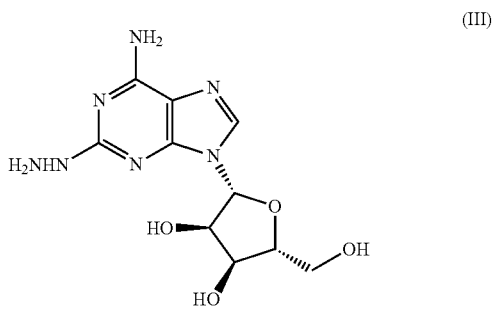

(III)

with ethyl 2-formyl-3-oxopropanoate in a suitable solvent and reaction temperature to obtain a compound of the formula (II). An example of a suitable solvent is water. The reaction temperature may be in the range of 25 to 80° C.

The presently disclosed processes provide pharmaceutically acceptable regadenoson in large quantities with good yield and high purity.

In further embodiments a process for making a novel polymorph of regadenoson is provided.

In one embodiment, a process for the preparation of polymorph (H) includes azeotropic distillation of the compound of Formula (I) [(1-{9-[4S, 2R, 3R, 5R)-3,4-dihydroxy-5-(hydroxymethyl)oxalan-2-yl]-6-aminopurin-2-yl] pyrazol-4-yl)-N-methylcarboxamine] in a suitable organic solvent medium and reaction temperature. An example of a suitable organic solvent is n-butanol. A suitable temperature may be in the range of 80-120° C.

Another solvent which may be employed for preparation of regadenoson polymorph H is ammonical methanol without azeotropic distillation. A suitable temperature range for this process is anywhere from 0-64° C.

The present inventors have discovered a novel polymorph which is easy to synthesize, highly reproducible and highly stable.

In one embodiment a polymorph H of formula (I) [(1-(9-[4S, 2R, 3R, 5R)-3,4-dihydroxy-5-hydroxymethyl)oxalan- 2-yl]-6-aminopurin-2-yl]pyrazol-4-yl)-N-methylcarboxamine] has a novel X-ray diffraction pattern as shown in FIG. 1.

In one embodiment the XRPD pattern of form H exhibits a characteristic peak at 25.52±0.2 (°2θ). In another embodiment the XRPD pattern of form H exhibits a characteristic peak at 6.16±0.2 (°2θ) and in still another embodiment the XRPD pattern of form H exhibits a characteristic peak at 10.31±0.2 (°2θ). Preferably, the XRPD pattern of form H exhibits characteristic peaks at 6.16 and 25.52±0.2 (°2θ). The XRPD pattern of form H may comprise peaks at 6.16, 10.31, 10.72 and 25.52±0.2 (°2θ).

In still further embodiments, the novel polymorphic form H of regadenoson is characterized by a powder X-ray diffractogram comprising peaks at one or more of 6.16, 10.31, 10.72, 12.38, 16.37, 21.57, 22.59, 25.52, 26.28, and 27.76±0.2 (°2θ), measured with a Cu-Kα irradiation (1.54060 Å).

In another embodiment a polymorph H of formula (I) [(1-{9-[4S, 2R, 3R, 5R)-3,4-dihydroxy-5-hydroxymethyl)oxalan-2-yl]-6-aminopurin-2-yl]pyrazol-4-yl)-N-methylcarboxamine] shows a marked endotherm in the range of 265-280° C. according to differential scanning calorimetry (DSC) as shown in FIG. 2.

In another embodiment a polymorph H of formula (I) [(1-(9-[4S, 2R, 3R, 5R)-3,4-dihydroxy-5-hydroxymethyl)oxalan-2-yl]-6-aminopurin-2-yl]pyrazol-4-yl)-N-methylcarboxamine] has a melting point in the range of 265-280° C.

In still further embodiments the present invention also provides a regadenoson drug substance comprising at least about 5%, preferably at least about 10%, of the novel polymorphic form of regadenoson as defined herein.

In yet another embodiment the regadenoson drug substance comprises at least about 50%, more preferably at least about 70%, of the novel polymorphic form of regadenoson as defined herein. In another embodiment substantially all or all (100%) of the regadenoson in the regadenoson drug substance is present in the novel polymorphic form H. "Substantially all" is meant to refer to a regadenoson drug substance comprising form H, wherein at least about 80%, preferably at least about 90%, more preferably at least about 95% of the regadenoson is present as form H.

In yet a further embodiment a pharmaceutical composition comprising the polymorphic form H of regadenoson is provided.

BRIEF DESCRIPTION OF THE DRAWINGS

For the purposes of illustration, there are forms shown in the drawings that are presently preferred, it being understood, however, that the invention is not limited to the precise arrangements and instrumentalities shown.

DETAILED DESCRIPTION OF THE PRESENT INVENTION

Figure 1:
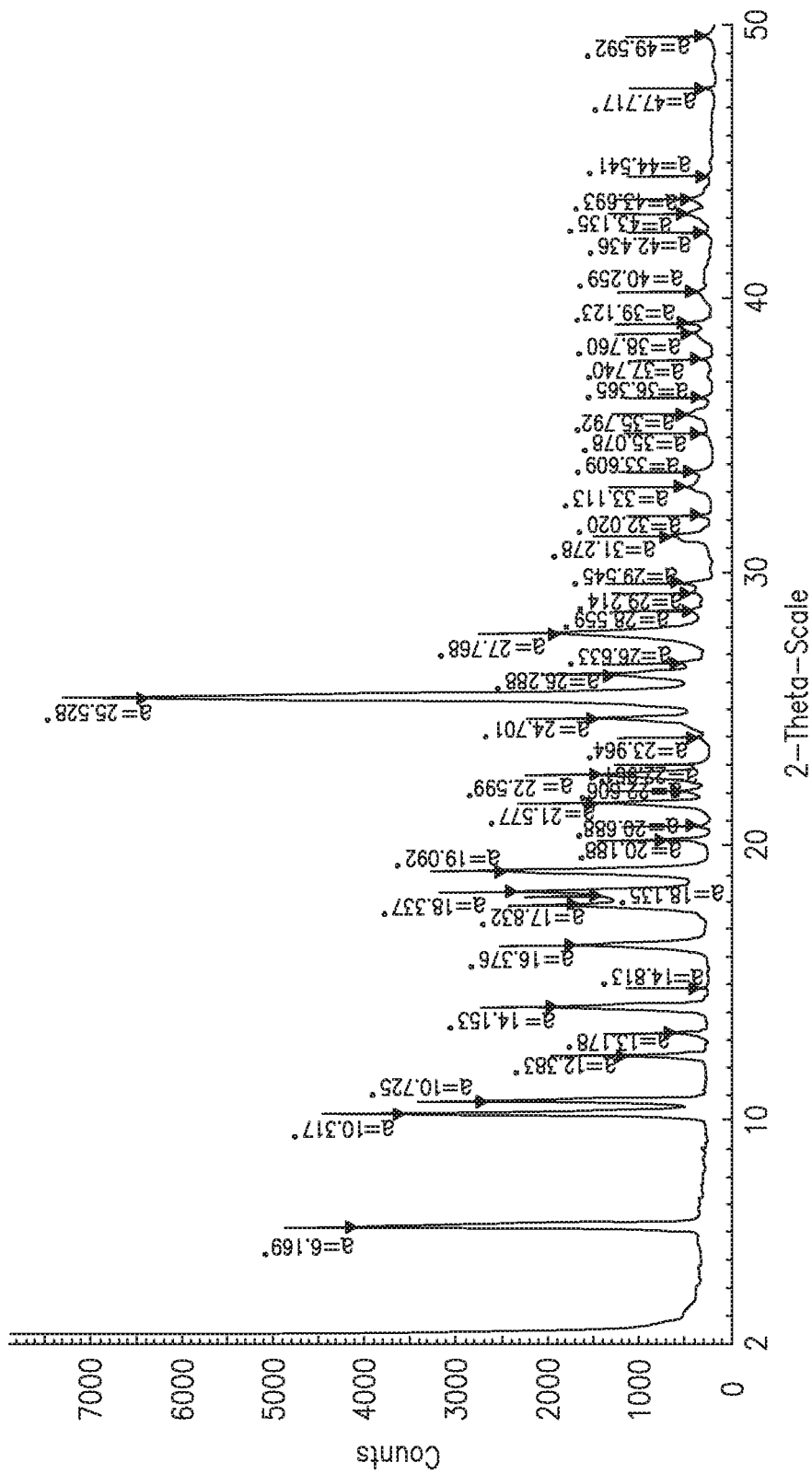
FIG. 1 is a graphical depiction of X-ray diffraction data (XRPD) of a novel polymorph of regadenoson according to an embodiment of the present disclosure.

The present invention provides novel processes for manufacturing regadenoson which involve the preparation of an intermediate ethyl 1-(6-amino-9-((2R,3R, 4S, 5R)-3,4-dihydroxy-5-(hydroxymethyl)tetrahydrofuran-2-yl)-9H-purin-2-yl)-1H-pyrazole-4-carboxylate and its subsequent condensation with aqueous methylamine to obtain regadenoson.

In one embodiment a synthetic route is described in Scheme 1.

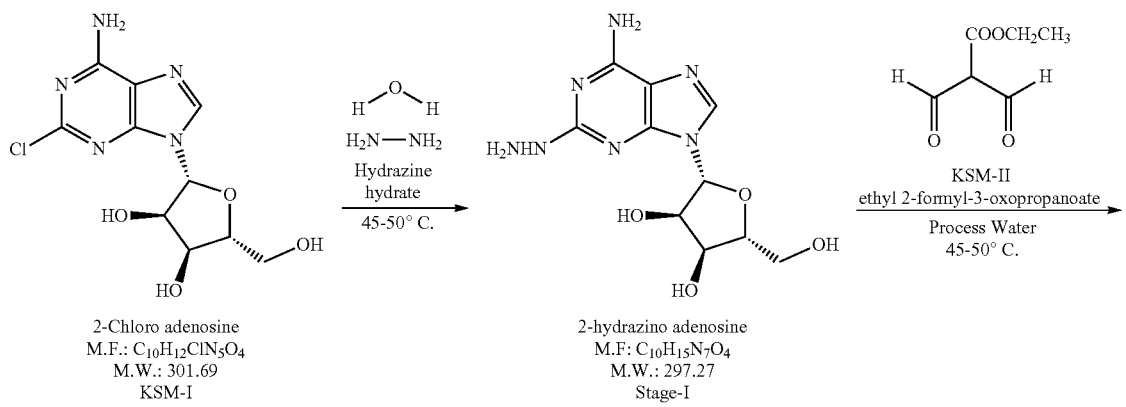

-continued

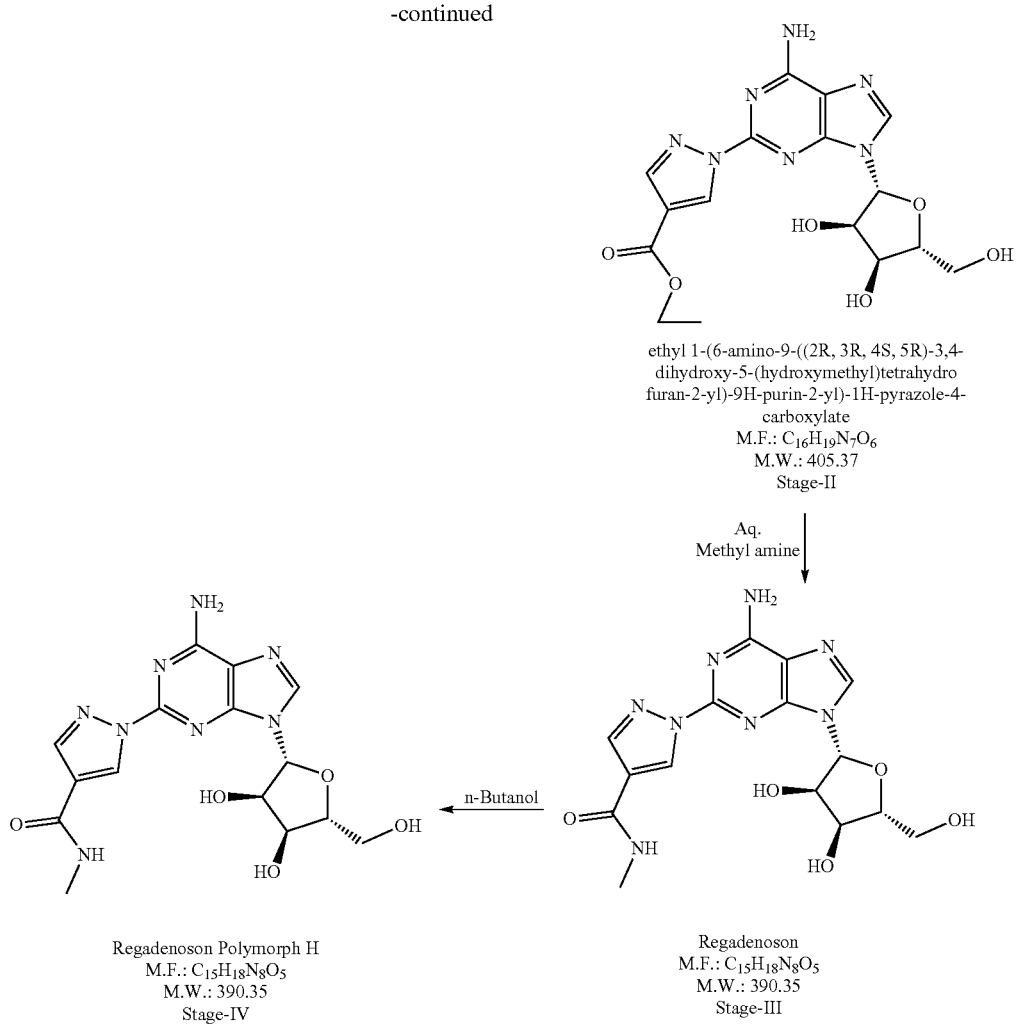

ethyl 1-(6-amino-9-((2R, 3R, 4S, 5R)-3,4-
dihydroxy-5-(hydroxymethyl)tetrahydro
furan-2-yl)-9H-purin-2-yl)-1H-pyrazole-4-
carboxylate
M.F.: $C_{16}H_{19}N_7O_6$
M.W.: 405.37
Stage-II Aq. Methyl amine Regadenoson
M.F.: $C_{15}H_{18}N_8O_5$
M.W.: 390.35
Stage-III n-Butanol Regadenoson Polymorph H
M.F.: $C_{15}H_{18}N_8O_5$
M.W.: 390.35
Stage-IV The presently disclosed processes for making regadenoson and intermediates thereof employ green processes which do not involve any organic solvents. For example, some of the presently disclosed processes employ water as a solvent in the preparation of intermediates as well as the final regadenoson product. The use of green processes is well emphasized and very much appreciated in all industrial applications. Thus the disclosed processes for making regadenoson and the intermediates thereof are highly novel and industrially useful.

Prior art processes for making regadenoson generally are not "green" and are not well-suited for use on an industrial scale.

For example, the preparation of the intermediate ethyl 1-(6-amino-9-((2R,3R, 4S, 5R)-3,4-dihydroxy-5-(hydroxymethyl) tetrahydrofuran-2-yl)-9H-purin-2-yl)-1H-pyrazole-4-carboxylate as described in prior art methods, such as in WO2007092372, where exclusively ethanol is involved, are all organic solvent-based methods of making regadenoson and intermediates thereof.

Moreover, U.S. Pat. No. 6,403,567 describes the preparation of regadenoson by condensing the precursor

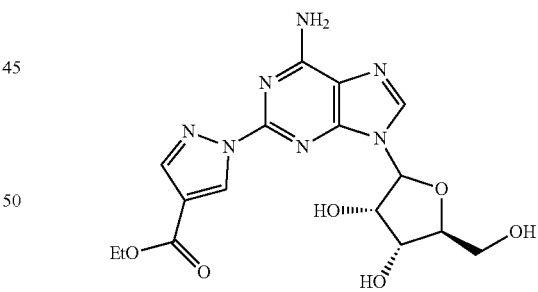

with aqueous methylamine. This process can generate impurities difficult to remove by conventional crystallisation methods, thus requiring laborious and time consuming column chromatographic techniques or preparative methods to isolate a pure product.

WO2013/026424 discloses using alcoholic solution of methylamine but it is not fully free from the impurities issues mentioned above.

U.S. Pat. No. 6,514,949 discloses a method of making regadenoson by a cross coupling of 2-iodoadenosine and 4-pyrazole carboxylic acid. Purification of the product prepared by this method involves column isolation techniques which are not cost effective and not easily scalable.

WO2012/149196 discloses a method involving cross coupling of 2-haloadenosine and 4-pyrazole carboxylic acid using a copper complex.

WO2007092372 discloses the use of ethanol solvent for the preparation of regadenoson intermediates which on further reaction with aqueous methylamine gives the final product regadenoson.

The presently disclosed processes overcome all the drawbacks of the aforementioned processes at least insofar as they are free from organic solvents, economical, scalable and environmentally friendly.

Novel Polymorph

Other aspects disclosed herein include the preparation of a novel polymorph of regadenoson.

Literature describes various polymorphs of regadenoson and methods of preparing these polymorphs. For example, WO 2008/143667 describes polymorphs A, B, C and the amorphous form and the method of preparation. Polymorph D is mentioned in WO2012/149196, while Polymorphs E, F, and G are mentioned in US 2014/0323712 A1 as well as in WO 2014/167046 A1.

The disclosed new polymorph (referred to herein as polymorph H) is in one embodiment prepared by a Dean-Stark method of removal of water using n-butanol as a solvent. Reciystallization of regadenoson using n-butanol surprisingly results in a new polymorphic form of regadenoson.

In another embodiment recrystallization of regadenoson using ammonical methanol surprisingly results in regadenoson polymorph H.

The novel polymorphic nature of the product is confirmed by X-ray diffraction (XRPD) differential scanning calorimetry (DSC) and thermal analysis. The novel polymorphic form H of regadenoson according to the present invention has at least one of the following characteristics:
a powder X-ray diffraction spectrum comprising a peak at least one of the following ° 2θ angles (±0.2); 6.16, 10.31, 10.72 and/or 25.52±0.2 (°2θ), as measured with Cu-Kα irradiation (1.54060 Å); a differential scanning calorimetry (DSC) peak within the range of 265-280° C. measured with a heating rate of 10° C./min; and/or a melting point in the range of 265-280° C.

In one embodiment the novel polymorphic form of regadenoson is characterized by two, three or four of the following powder X-ray diffraction peaks (°2θ) (±0.2): 6.16, 10.31, 10.72, 12.38, 16.37, 21.57, 22.59, 25.52, 26.28, and 27.76, measured with a Cu-Kα irradiation (1.54060 Å).

The temperatures given herein for DSC include variations of ±2° C. due to measurement inaccuracies. The ° 2θ angles given herein include variations of ±0.2 due to measurement inaccuracies of the powder X-ray diffraction experiments.

The present invention also provides a regadenoson drug substance comprising at least about 5%, preferably at least about 10%, of the novel polymorphic form of regadenoson as defined herein.

In a preferred embodiment the regadenoson drug substance comprises at least about 50%, more preferably at least about 70%, of the novel polymorphic form of regadenoson as defined herein. In another embodiment substantially all or all (100%) of the regadenoson in the regadenoson drug substance is present in the novel polymorphic form H. "Substantially all" is meant to refer to a regadenoson drug substance comprising form H, wherein at least about 80%, preferably at least about 90%, more preferably at least about 95% of the regadenoson is present as form (H).

In the context of the present application all percentages are given by weight unless otherwise indicated.

Furthermore, the present invention provides a pharmaceutical composition which comprises the novel polymorphic form H of regadenoson as defined above and at least one pharmaceutically acceptable excipient. Pharmaceutical preparations containing the novel polymorphic form H regadenoson such as injections, etc. are prepared according to methods commonly known in the state of the art.

EXAMPLES—SCHEME I

Example 1: Preparation of 2-Hydrazino Adenosine

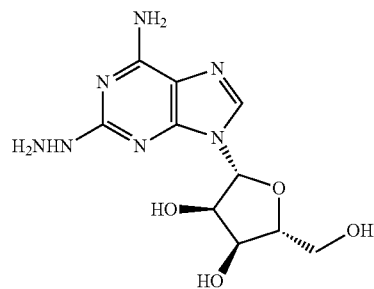

Hydrazine hydrate (80% in water) solution (500.00 mL) was heated at 45° C. to 50° C. and charged 2-chloroadenosine (100.00 gm) at 45° C. to 50° C. in one lot. Heated reaction mass at 45° C. to 50° C. for 6-8 hours (until 2-chloro adenosine consumed completely) and reaction mass monitored by HPLC. Cooled reaction mass to 25-30° C. and started addition of 30% NaCl solution into reaction mass at 25-30° C. Stirred reaction mass at 25-30° C. overnight. Filtered the reaction mass and washed with process water (100.00 mL×3), Suction dried well. Dried at 50-60° C. Dry Weight: 80.00-85.00 gm (% of Yield: −80-87%)

Example 2: Preparation of ethyl 1-(6-amino-9-((2R, 3R, 4S, 5R)-3,4-dihydroxy-5-hydroxymethyl) tetrahydrofuran-2-yl)-9H-purin-2-yl)-1H-pyrazole-4-carboxylate

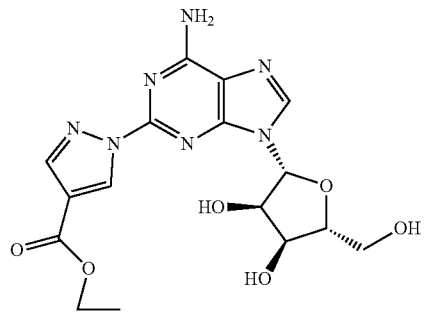 [SMILES: CCOC(=O)c1cnn(-c2nc(N)c3ncn([C@@H]4O[C@H](CO)[C@@H](O)[C@H]4O)c3n2)c1]

A mixture of 2-hydrazino adenosine (100.00 gm), process water (4000.00 mL) and (ethoxy carbonyl) malondialdehyde (55.75 gm) was stirred until reaction mass became clear and filtered immediately through Celite bed, washed bed by process water. Heated filtrate at 45-50° C. until reaction complies (monitored by HPLC). Cooled the reaction mass at 25-30° C. and stirred for 4-5 hours. Filtered the reaction mass and washed with process water (100.00 mL×3). Suction dried well. Dried at 50-60° C. Dry Weight: 115.00 gm-129.50 gm (% of Yield: ~85-95%).

Example 3: Preparation of Regadenoson

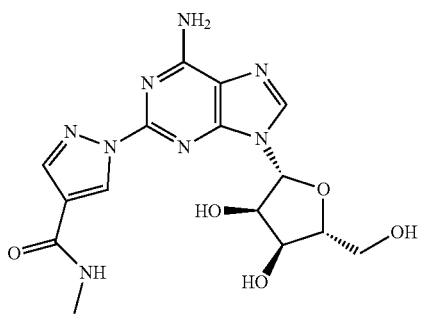 [SMILES: CNC(=O)c1cnn(-c2nc(N)c3ncn([C@@H]4O[C@H](CO)[C@@H](O)[C@H]4O)c3n2)c1]

A mixture of the product Stage II (100.00 gm) and methyl amine solution (40% in water) was stirred at 25-30° C. for 24 hours (until it complies monitored by HPLC), then started purging of N2 gas to reduce pH. Filtered the reaction mass and washed by process water (100.00 mL×3). Suction dried well. Dried at 50-60° C. Dry Weight: 60.00 gm-70.00 gm (% of Yield: ~60.00-70.00%)

Example 4: Preparation of Regadenoson New Polymorph H

Regadenoson of Example 3 (100.00 gm) and n-butanol (2000.00 mL) were heated and refluxed azeotropically for 2 days. Cooled the reaction mass at 25-30° C. Stirred the reaction mass at 25-30° C. for 1 hour. Filtered the reaction mass and washed with n-butanol (100.00 mL) Suction dried well. Dried at 50-60° C. Dry Weight: 80.00 gm-90.00 gm (% of Yield: ~80-90%)

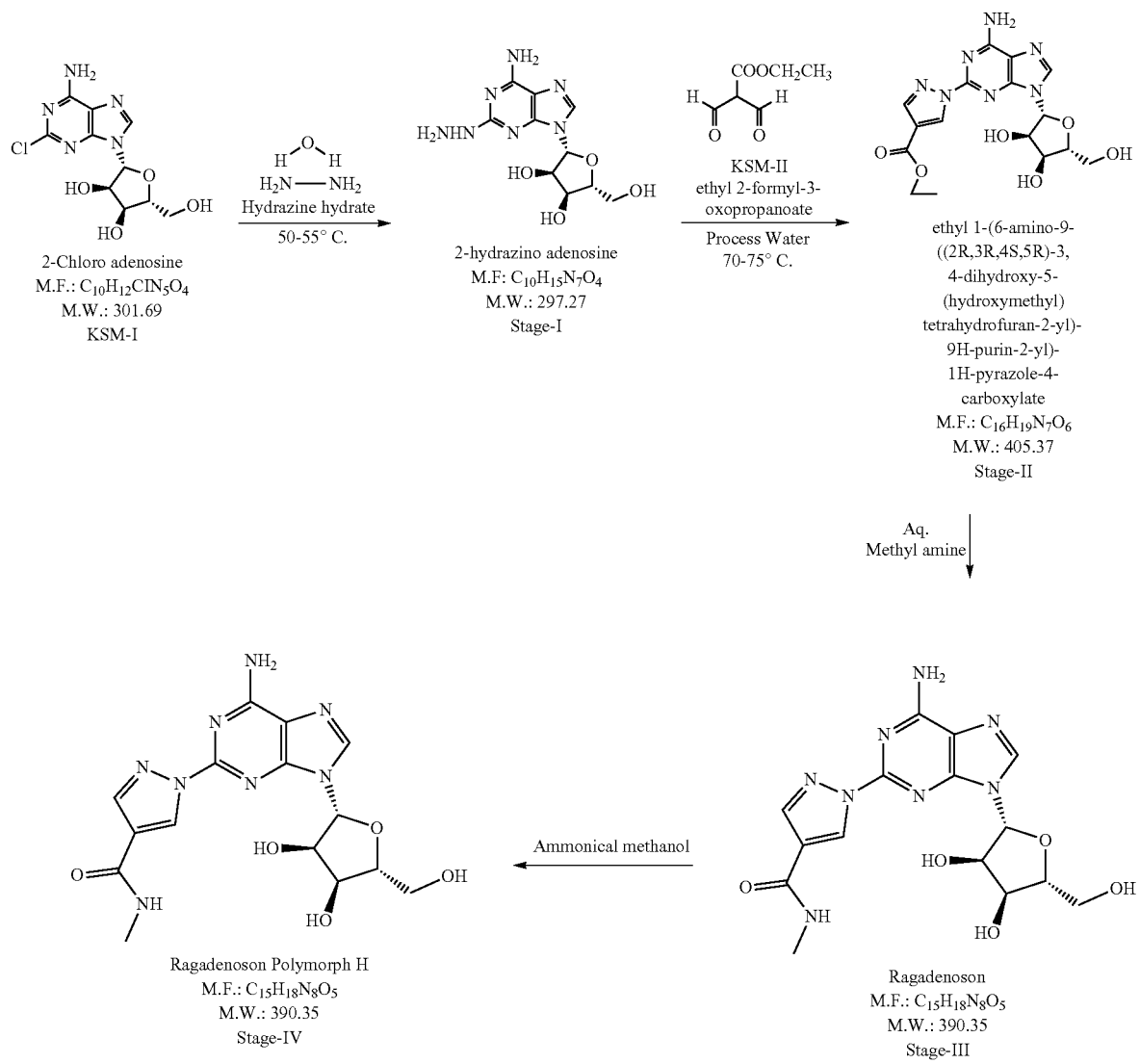

Scheme II

EXAMPLES FOR SCHEME II

Example 5: Preparation of 2-Hydrazino Adenosine

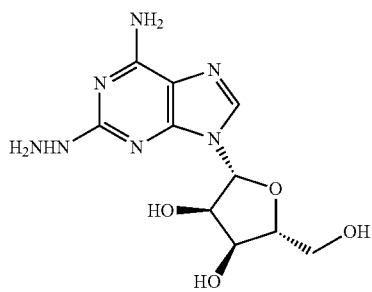

Hydrazine hydrate (80% in water) solution (500.00 mL) was heated at 50° C. to 55° C. and charged 2-chloroadenosine (100.00 gm) at 50° C. to 65° C. in one lot. Heated reaction mass at 50° C. to 65° C. for 30 minutes (until 2-chloro adenosine consumed completely) and reaction mass monitored by HPLC. Distilled out reaction mass completely and stripped out by process water. Charged process water (500 mL) and heated the reaction mass at 50-55° C. for 30 minutes. Cooled reaction mass to 25-30° C. and stirred for 1 hour. Filtered the reaction mass and washed with process water (100.00 mL×3), Suction dried well. Dried at 50-60° C. Dry Weight: 75.00-85.00 gm (% of Yield: –75-85%)

Example 6: Preparation of ethyl 1-(6-amino-9-((2R, 3R, 4S, 5R)-3,4-dihydroxy-5-hydroxymethyl) tetrahydrofuran-2-yl)-9H-purin-2-yl)-1H-pyrazole-4-carboxylate

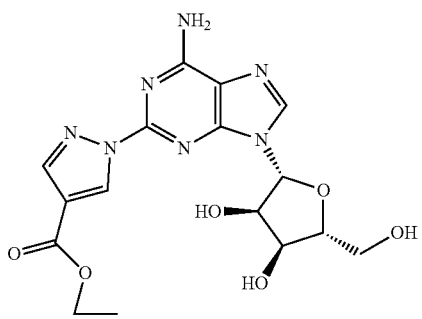 [SMILES: CCOC(=O)c1cnn(-c2nc(N)c3ncn([C@@H]4O[C@H](CO)[C@@H](O)[C@H]4O)c3n2)c1]

A mixture of 2-hydrazino adenosine (100.00 gm), process water (4000.00 mL) and (ethoxy carbonyl) malondialdehyde (55.75 gm) was heated at 70-75° C. until reaction complies (monitored by HPLC). Cooled the reaction mass at 25-30° C. and stirred for 1-2 hours. Filtered the reaction mass and washed with process water (100.00 mL×3). Suction dried well. Dried at 50-60° C. Dry Weight: 115.00 gm-129.50 gm (% of Yield: –85-95%).

Example 7: Preparation of Regadenoson

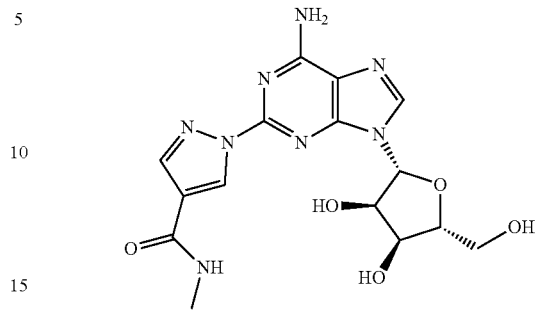

A mixture of the product Stage II (100.000 gm) and methyl amine solution (40% in water) was stirred at –10 to 0° C. for 3 hours and 5-10° C. for 1.5 hours (until it complies, monitored by HPLC), then vacuum was applied for 1-5 hours, charged process water (300 mL), heated at 50-55° C. for 1 hour, cooled the reaction mass at 25-30° C., stirred for 1 hour. Filtered the reaction mass and washed by process water (100.00 mL×3). Suction dried well. Dried at 50-60° C. Dry Weight: 80.00 gm-90.00 gm (% of Yield: –80.00-90.00%)

Example 8: Purification of Regadenoson

Purified sample in DMF and acetone mixture.

Example 9: Preparation of Regadenoson New Polymorph H

A compound of Example 7 (100.00 gm) and Ammonical methanol (3000.00 mL) were heated at 45-55° C. Cooled the reaction mass at 25-30° C. Stirred the reaction mass at 25-30° C. for 1 hour. Filtered the reaction mass and washed with Ammonical methanol (100.00 mL) Suction dried well. Dried at 50-60° C. Dry Weight: 80.00 gm-90.00 gm (% of Yield: –80-90%)

Example 10

A mixture of the product Stage II (100.00 gm) and methyl amine solution (40% in water) was stirred at –7 to –5° C. initially and later stirred at –7° C. to –3° C. for 5 hours, at 0-5° C. for 1 hour and at 25-30° C. for 1 hour (until it complies monitored by HPLC), then vacuum was applied until 24 vol. of reaction mass remained. Heated the reaction mass at 50-55° C. for 1 hour, cooled the reaction mass at 25-30° C., stirred for 1 hour. Filtered the reaction mass and washed by process water (100.00 mL×3). The wet cake was slurried into acetone (1500 mL) at RT. Filtered reaction mass. The wet cake was purified in DMF: Acetone solvent, filtered, and the wet cake was refluxed in toluene azeotropically. The wet cake was heated in ammonical methanol at 40-60° C. and stirred for 1 hour. Cooled to room temperature and filtered the reaction mass. Dried at 50-60° C. Dry Weight: 30.00 gm-60.00 gm.

Characterization of form H is accomplished using techniques known to those of skill in the art. Specifically, verification that form (H) is present can be performed using techniques such as differential scanning calorimetry (DSC), powder X-ray diffraction (XRPD) and melting point, infrared (IR) spectroscopy, solid state nuclear magnetic resonance (NMR) spectroscopy and Raman spectroscopy are also useful in distinguishing polymorphs. One or more of the foregoing techniques can be used to identify a polymorphic form of regadenoson.

XRPD Data of Regadenoson Prepared Using Ammonical Methanol

A sample made using Scheme 11 was subjected to Powder X-Ray Diffraction (XRPD) analysis measured with a Cu-Kα irradiation (1.54060 Å). With reference to Table 1 and FIG. 1, XRPD data show a novel polymorph of regadenoson prepared in ammonical methanol.

TABLE 1

| Sr. No. | XRPD 2θ value | d-Spacing | Intensity |
|---|---|---|---|
| 01 | 6.16 | 14.31 | 63.6 |
| 02 | 10.31 | 8.56 | 55.0 |
| 03 | 10.72 | 8.24 | 41.1 |
| 04 | 12.38 | 7.14 | 16.8 |
| 05 | 16.37 | 5.40 | 26.1 |
| 06 | 21.57 | 4.11 | 77.1 |
| 07 | 22.59 | 3.93 | 21.4 |
| 08 | 25.52 | 3.48 | 100.0 |
| 09 | 26.28 | 3.38 | 18.7 |
| 10 | 27.76 | 3.21 | 29.1 |

DSC Data for Regadenoson Prepared Using Ammonical Methanol

DSC was conducted using a Q2000 Differential Scanning Calorimeter V24.10 from TA Instruments of New Castle Del. One of skill in the art would readily be able to determine the conditions necessary to obtain a DSC thermogram of form H. A variety of differential scanning calorimeters are available to those of skill in the art which may use temperatures of about 25° C. to about 320° C., in particular about 30° C. to about 300° C. and temperature increases at various rates including 1° C./min, 10° C./min, 20° C./min, among other conditions. One skilled in the art would recognize that the peak positions in the DSC thermogram can vary depending upon kinetic factors such as, for example, heating rate and particle size.

Figure 2:
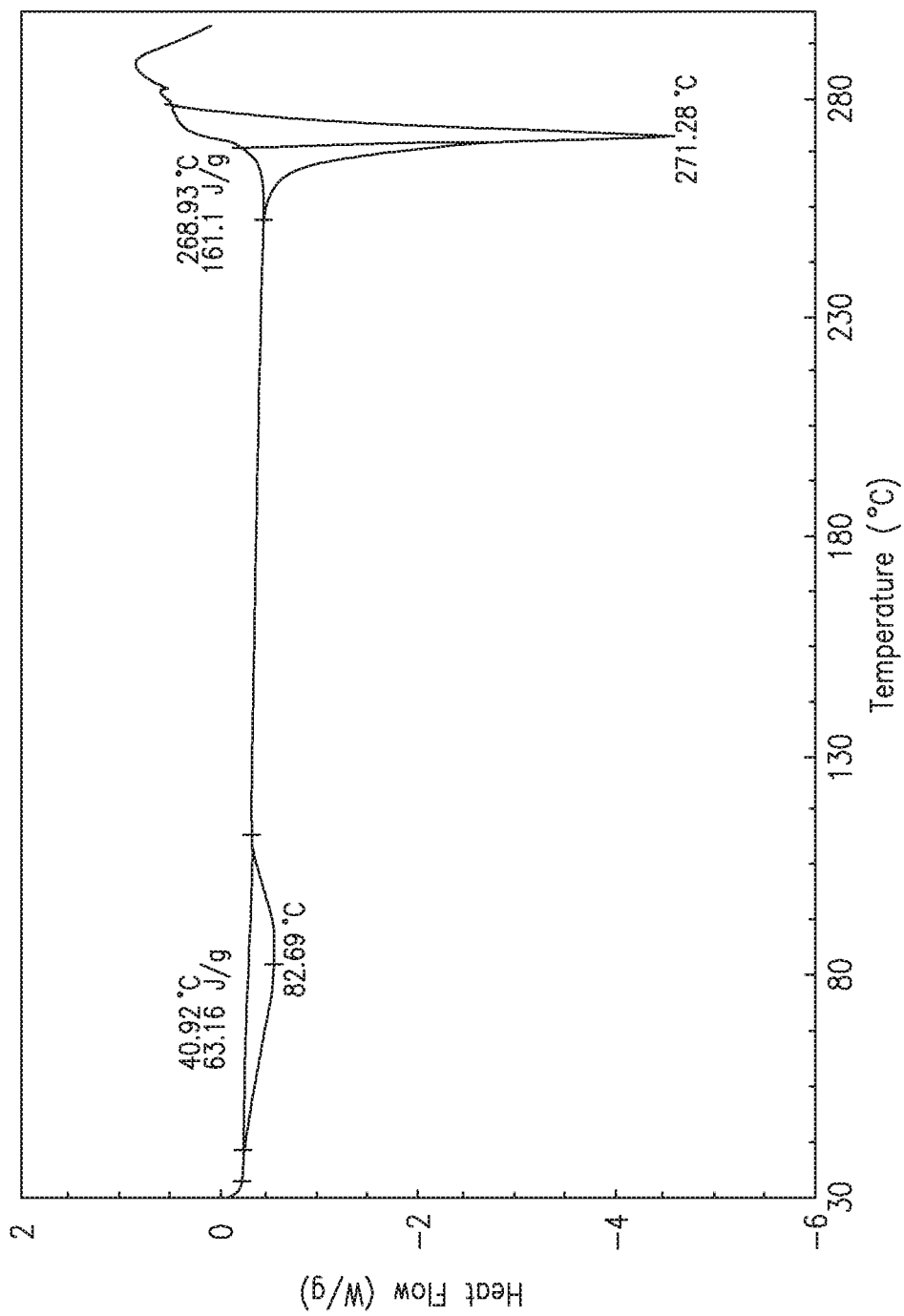
FIG. 2 is a graphical depiction of differential scanning calorimetry (DSC) data of a novel polymorph of regadenoson according to an embodiment of the present disclosure.

An 8.0230 mg sample made using Scheme II was analysed using (30-300)° C.-Ramp-10° C./min. A DSC thermogram of form H is provided in FIG. 2, With reference to FIG. 2, DSC data for the batch reveals a characteristic DSC peak at 271.28° C. (between: 265-280° C.). DSC analysis of this form clearly shows a sharp endothermic signal in the DSC histogram which further confirms the new polymorphic nature of the product.

Although the compositions and methods of the present disclosure have been described with reference to exemplary embodiments thereof, the present disclosure is not limited thereby. Indeed, the exemplary embodiments are implementations of the disclosed compositions and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

What is claimed is:

1. A polymorphic form of regadenoson characterized by
   (a) a powder X-ray diffraction (XRPD) spectrum comprising peaks at the following angles: 6.16, 10.31, 10.72 and 25.52±0.2 (°2θ), and further comprising one or more peaks selected from the group consisting of 12.38, 16.37, 21.57, 22.59, 26.28, and 27.76±0.2 (°2θ), measured with a Cu-Kα irradiation;
   (b) a differential scanning calorimetry (DSC) peak in the range of 265-280° C. measured with a heating rate of 10° C./min; and
   (c) the absence of an exothermic DSC peak in the range of about 30° C. up to the polymorphic form melting point as measured with a heating rate of 10° C./min.

2. A regadenoson drug substance comprising about 5% by weight or more of the polymorphic form of regadenoson according to claim 1.

3. A regadenoson drug substance comprising about 50% by weight or more of the polymorphic form of regadenoson according to claim 1.

4. A regadenoson drug substance comprising about 95% by weight or more of the polymorphic form of regadenoson according to claim 1.

5. A pharmaceutical composition comprising the polymorphic form of regadenoson according to claim 1.

6. The polymorphic form of regadenoson according to claim 1 characterized by a powder X-ray diffractogram comprising peaks at 6.16, 10.31, 10.72, 12.38, 16.37, 21.57, 22.59, 25.52, 26.28, and 27.76±0.2 (°2θ), measured with a Cu-Kα irradiation.

7. A regadenoson drug substance comprising about 5% by weight or more of the polymorphic form of regadenoson according to claim 6.

8. A regadenoson drug substance comprising about 50% by weight or more of the polymorphic form of regadenoson according to claim 6.

9. A regadenoson drug substance comprising about 95% by weight or more of the polymorphic form of regadenoson according to claim 6.

10. A pharmaceutical composition comprising the polymorphic form of regadenoson according to claim 6.

* * * * *